(12) United States Patent
Duhay et al.

(10) Patent No.: US 8,449,466 B2
(45) Date of Patent: May 28, 2013

(54) SYSTEM AND METHOD FOR LOCATING MEDICAL DEVICES IN VIVO USING ULTRASOUND DOPPLER MODE

(75) Inventors: Francis G. Duhay, Irvine, CA (US); David Zollinger, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 435 days.

(21) Appl. No.: 12/789,156

(22) Filed: May 27, 2010

(65) Prior Publication Data

US 2010/0305432 A1    Dec. 2, 2010

Related U.S. Application Data

(60) Provisional application No. 61/182,064, filed on May 28, 2009.

(51) Int. Cl.
*A61B 8/00* (2006.01)

(52) U.S. Cl.
USPC ............ 600/439; 600/407; 600/437; 600/462

(58) Field of Classification Search
USPC ................. 600/407, 437, 441, 443, 446, 447, 600/459, 462; 601/2, 46, 57
See application file for complete search history.

(56) References Cited

U.S. PATENT DOCUMENTS

| | | | |
|---|---|---|---|
| 4,694,434 A | 9/1987 | Von Ramm et al. | |
| 4,974,590 A * | 12/1990 | Saito | 600/462 |
| 5,054,491 A * | 10/1991 | Saito et al. | 600/109 |
| 5,095,910 A | 3/1992 | Powers | |
| 5,104,407 A | 4/1992 | Lam et al. | |
| 5,108,420 A | 4/1992 | Marks | |
| 5,329,927 A | 7/1994 | Gardineer et al. | |
| 5,343,865 A | 9/1994 | Gardineer et al. | |
| 5,451,235 A | 9/1995 | Lock et al. | |
| 5,546,807 A | 8/1996 | Oxaal et al. | |
| 5,879,366 A | 3/1999 | Shaw et al. | |
| 5,921,933 A | 7/1999 | Sarkis et al. | |
| 5,961,440 A | 10/1999 | Schweich et al. | |

(Continued)

FOREIGN PATENT DOCUMENTS

| EP | 0453251 A1 | 10/1991 |
|---|---|---|
| GB | 2287319 A | 9/1995 |

OTHER PUBLICATIONS

International Search Report from corresponding International Application No. PCT/US2010/036637 mailed Jan. 3, 2011.

(Continued)

*Primary Examiner* — James Kish
*Assistant Examiner* — Michael N Fisher
(74) *Attorney, Agent, or Firm* — AnnMarie Kaiser; Guy Cumberbatch

(57) ABSTRACT

A system for locating a medical device in vivo includes an ultrasound scanner having a scan head and being capable of operating in a 3D Doppler mode, a medical device having a distal end configured to be inserted in vivo, and a vibratory element coupled to the medical device to induce vibrations in the first distal end. When the scan head is positioned over the distal end inserted in vivo to obtain scan data of the tissue volume, the ultrasound scanner is configured to generate 3D Doppler data in the form of a plurality of slices from the scan data and to identify a location of the distal end within the slices based upon localized data within one of the slices meeting predetermined criteria.

18 Claims, 6 Drawing Sheets

U.S. PATENT DOCUMENTS

| | | | |
|---|---|---|---|
| 5,967,985 A | 10/1999 | Hayakawa | |
| 6,050,936 A | 4/2000 | Schweich et al. | |
| 6,106,473 A | 8/2000 | Violante et al. | |
| 6,146,329 A | 11/2000 | Hayakawa | |
| 6,182,664 B1 | 2/2001 | Cosgrove | |
| 6,214,029 B1 | 4/2001 | Thill et al. | |
| 6,332,893 B1 | 12/2001 | Mortier et al. | |
| 6,336,899 B1 | 1/2002 | Yamazaki | |
| 6,402,680 B2 | 6/2002 | Mortier et al. | |
| 6,506,156 B1 | 1/2003 | Jones et al. | |
| 6,577,904 B1 | 6/2003 | Zhang et al. | |
| 6,602,288 B1 | 8/2003 | Cosgrove et al. | |
| 6,610,016 B1 | 8/2003 | Violante et al. | |
| 6,723,038 B1 | 4/2004 | Schroeder et al. | |
| 6,726,717 B2 | 4/2004 | Alfieri et al. | |
| 6,749,630 B2 | 6/2004 | McCarthy et al. | |
| 6,836,054 B2 * | 12/2004 | Boyd | 310/316.01 |
| 6,889,552 B2 * | 5/2005 | Nguyen et al. | 73/632 |
| 7,229,413 B2 | 6/2007 | Violante et al. | |
| 7,329,225 B2 | 2/2008 | Smith et al. | |
| 2002/0173720 A1 | 11/2002 | Seo et al. | |
| 2004/0230111 A1 * | 11/2004 | Smith et al. | 600/407 |
| 2007/0112422 A1 | 5/2007 | Dehdashtian | |
| 2008/0015437 A1 | 1/2008 | Hongou | |
| 2008/0294037 A1 | 11/2008 | Richter | |
| 2011/0105903 A1 | 5/2011 | Ohnuma | |

OTHER PUBLICATIONS

Supplementary Partial European Search Report in corresponding European Application No. 10781302.4 (PCT/US2010036637) dated Dec. 18, 2012.

* cited by examiner

SYSTEM AND METHOD FOR LOCATING MEDICAL DEVICES IN VIVO USING ULTRASOUND DOPPLER MODE

RELATED APPLICATION DATA

The present application claims priority under 35 U.S.C. §119(e) to U.S. Provisional Application No. 61/182,064 filed May 28, 2009.

BACKGROUND OF THE INVENTION

1. Field of the Invention

The field of the present invention is medical imaging, and in particular medical applications of Doppler mode ultrasound imaging.

2. Background

A major limitation to open- and closed-chest manipulation of an intact organ is the ability to visualize within the organ in real time. Current examples of modalities that allow real time imaging within an intact organ include fluoroscopy, computer assisted tomography, magnetic resonance imaging, and ultrasonography. Ultrasonography, or echocardiography (echo) as it applies to the ultrasonic imaging of the heart, is the most commonly applied diagnostic modality employed to acquire real time, structural images of the heart. Echo is able to acquire structural images with high spatial resolution and fidelity to accurately measure static and dynamic anatomic dimensions and configuration, and is also able to detect relative physical motion by exploiting the Doppler effect. Accordingly, echo is able to evaluate qualitative and quantitative hemodynamic flow, turbulence, and pressure. Based on a fluid's velocity, the echo image can be labeled to display a prespecified color. For example, a high velocity fluid jet associated with the narrowing of the aortic valve can be made to appear yellow or orange. Whereas, a low velocity jet associated with incompetence of the mitral valve can be made to appear blue or purple.

Despite its value in providing accurate static and dynamic structural and hemodynamic images, ultrasonography is limited in its ability to provide high precision images of certain medical devices, such as catheters, wires, or instruments. In part, this is because of the acoustic shadowing or artifacts that can be attributed to physical properties of these devices. For example, the body of a catheter within the heart is usually discernible by echo; however, identifying a specific physical location on the catheter—such as its tip—is problematic. To facilitate the precise identification of such physical attributes, attempts have been made to improve the echogenicity of the medical device, either by physically manipulating the surface characteristics of the device, or by introducing some form of contrast agent into, or around, the device, such as air.

One technique that has met with some success is the use of real-time Doppler mode ultrasound imaging (also known as B-mode ultrasound imaging). An early technique is found in U.S. Pat. No. 5,095,910, the disclosure of which is incorporated herein by reference in its entirety, which describes locating the tip of a biopsy needle through use of Doppler mode ultrasound imaging when the tip is oscillated in the longitudinal direction. Later developments include affixing a mechanical vibrator to the proximal end of a needle or cannula to provide longitudinal vibrations down the length of the shaft, such as is described in U.S. Pat. No. 5,343,865, the disclosure of which is incorporated herein by reference in its entirety. Alternatively, U.S. Pat. No. 5,329,927, the disclosure of which is incorporated herein by reference in its entirety, describes introducing transverse flexural vibrations in a biopsy needle to render the needle more visible using Doppler mode ultrasound imaging. A more recent development, described in U.S. Pat. No. 7,329,225, also incorporated by reference herein, employs a system to automatically track the tip of a shaft within a 3D ultrasound scan by identifying local maxima in the Doppler signal. However, additional benefits may still be obtained through use of Doppler mode ultrasound imaging for locating medical devices in vivo.

SUMMARY OF THE INVENTION

The present invention is directed toward a system and method for locating the distal end of a medical device in vivo. The system includes a medical device having a vibratory element affixed thereto, with the medical device being configured for performance of at least one of a minimally invasive medical procedure, a medical diagnosis, and monitoring internal tissue conditions. The scan head of an ultrasonic imaging system is placed over the body to generate real-time scan images that include the medical device. The imaging system, whether 2D or 3D, includes a Doppler mode, which generates coloration within the scan images to highlight the location of the medical device. Further, the Doppler mode coloration assigned to different Doppler signals may be adjusted to provide contrast between different parts of the medical device, when different parts are configured to vibrate with different frequencies, or between the medical device and hemodynamic flow, turbulence, or pressure in the surrounding tissues. Alternatively, or in combination, frequencies of vibration within the medical device, or within different parts of the medical device, may be adjusted to provide coloration contrast during Doppler mode ultrasound imaging.

In addition, the ultrasound scanner may be configured to utilize the Doppler mode coloration to identify a location of the distal end of the medical device within one of a plurality of scan data slices, wherein the slice including the distal end of the medical device includes localized data that meets predetermined criteria. This localized data may indicate that an object is moving above a predefined threshold value within a data slice, or alternatively, it may show a maximum rate of change within the data slices.

Accordingly, an improved system and method for locating the distal end of a medical device in vivo are disclosed. Advantages of the improvements will appear from the drawings and the description of the preferred embodiment.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
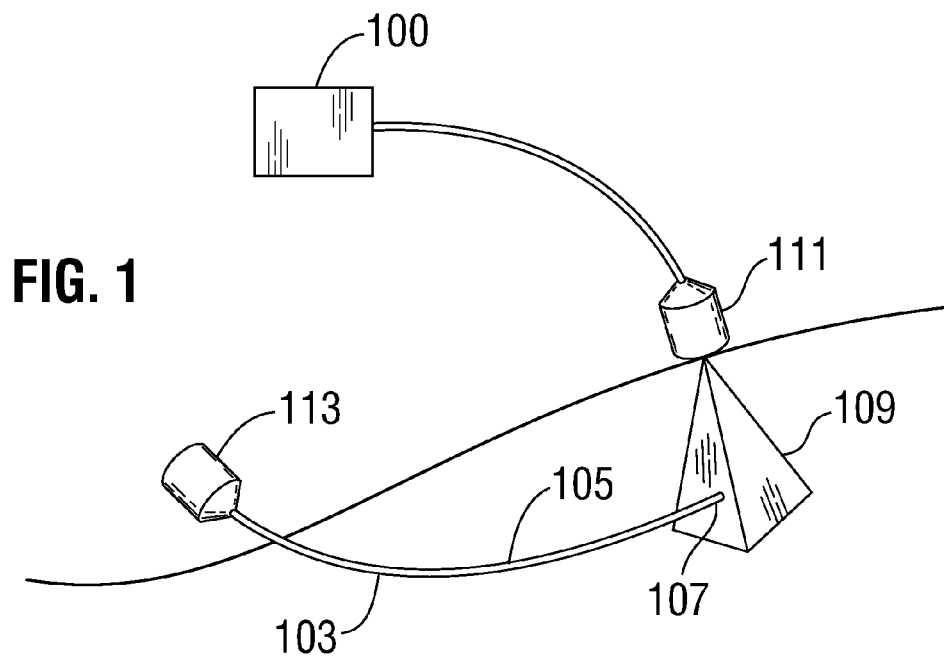
FIG. 1 schematically illustrates a system for locating the distal end of a medical device in vivo, with the device including a vibratory element external to the body.

Turning in detail to the drawings, FIG. 1 illustrates a FIG. 1 a real-time three-dimensional (3D) ultrasound scanner 100 used to scan an oscillating shaft of a medical device 103, such as a needle, a cannula, or the like, to provide real-time images that include the oscillating shaft in vivo. The medical device 103 includes, among other things, a shaft 105, which may be rigid or flexible, with a tip 107. Oscillations (or vibrations) are induced in both the shaft 105 and the tip 107 by the vibration module 113 affixed to the proximate end of the shaft 105. The medical device 103 is guided to anatomy of interest within a patient's body using images provided by the real-time 3D ultrasound scanner 100, which are obtained from echo data within the scan region 109 defined by the ultrasound transducer 111 which includes at least the tip 107. Further, the real-time 3D ultrasound scanner 100 is configured to operate in 3D Doppler mode in a manner that is well known to those of skill in the relevant arts. Oscillation of the shaft 105 makes the entire shaft 105 more discernable in Doppler mode images provided by the real-time 3D ultrasound scanner 100. Moreover, not only is the shaft 105 more discernable, but the tip 107 is particularly more discernable. Thus, the tip 125 may be more effectively guided using the real-time 3D ultrasound scanner 100.

It is known to provide the echo data as three dimensional, or volumetric, ultrasound images using two dimensional ultrasound transducer arrays. For example, U.S. Pat. No. 4,694,434 to von Ramm and Smith discloses a steered phased array acoustic imaging scanner that provides a pyramidal volumetric scan of a region using a two dimensional ultrasound transducer array. It will be understood that the real-time 3D ultrasound scanner 100 can be the type of scanner disclosed in U.S. Pat. No. 5,546,807 to Oxaal et al, the disclosure of which is incorporated herein by reference in its entirety. It will be further understood that Oxaal discloses the display of images obtained from a volumetric scanner in which slices of the region scanned can be displayed in real time, where the slices can be, what are sometimes referred to as, B-mode slices, C (Constant) slices, and I (Inclined) slices. It will be understood that although B-mode slices are illustrated in the figures, any of the above type slices can be used in embodiments according to the invention. Moreover, both 2D and 3D Doppler mode ultrasound scanners presently available in the marketplace allow the coloration of the Doppler mode images to be adjusted, so that image data which results from predefined ranges of Doppler data can be assigned desired colors. Thus, the Doppler mode images can be given any coloration desired, such that particular features seen within the images, including the features of the vibrating medical device in vivo, may be assigned particular colors within the images. As will become clear from the additional description below, this feature may be advantageously used in connection with vibrating medical devices when they are inserted or placed in vivo.

Figure 7A:
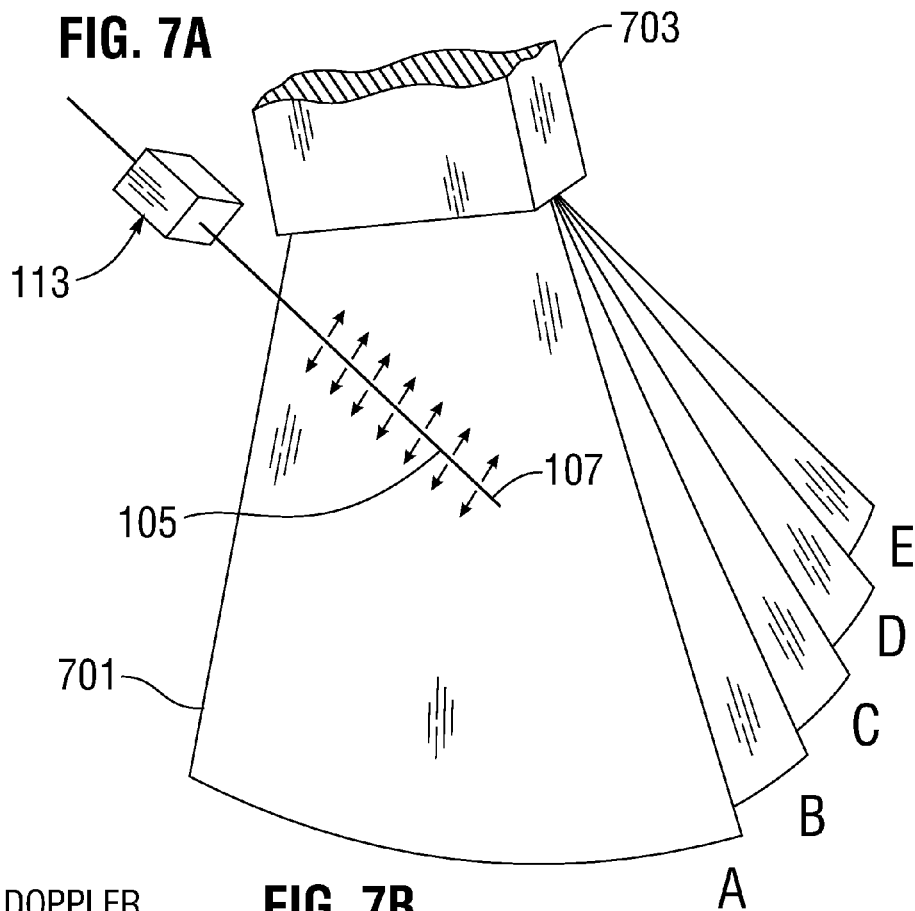
FIGS. 7A & 7B illustrate 3D ultrasound tracking, using Doppler mode, of a medical device in vivo.
Figure 7B:
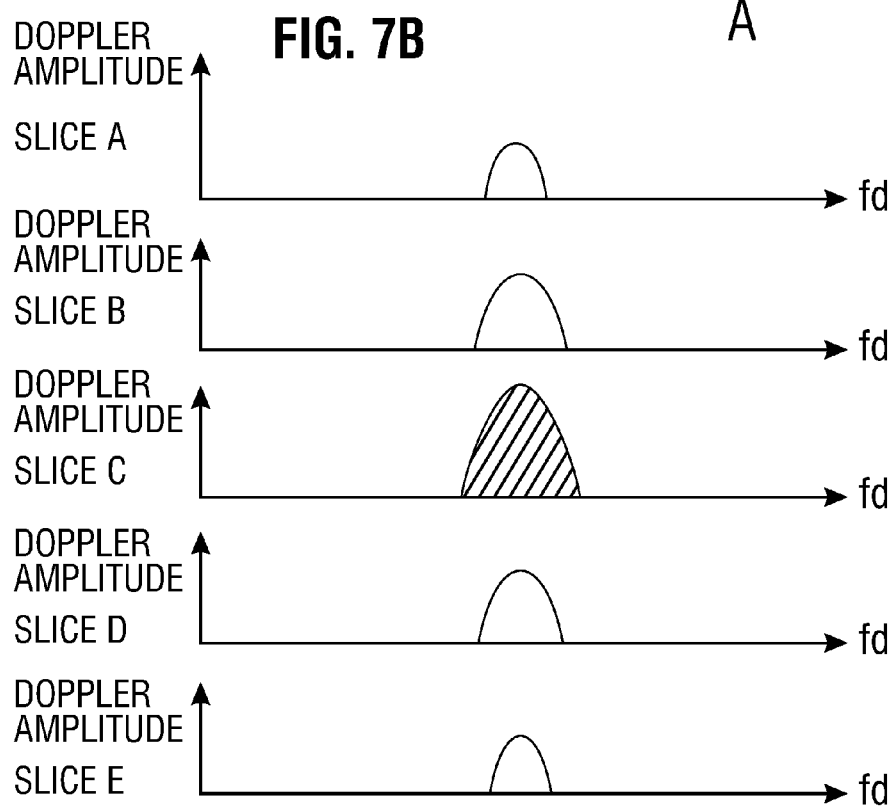

As is described in U.S. Pat. No. 7,329,225 and in U.S. Pat. No. 6,336,899, the disclosures of which are incorporated herein by reference in their entirety, data from a 3D Doppler mode ultrasound scanner may be used to automatically track the tip of the shaft in vivo. As is shown in FIG. 7A, the 3D echo data 701 includes data corresponding to the oscillating tip of the medical device. The Doppler mode ultrasound scanner processes the 3D echo data to obtain Doppler data for moving objects within the 3D echo image data—this includes the entire shaft 105 and tip 107, both of which are vibrating due to the attached vibration module 113. Furthermore, the real-time 3D ultrasound scanner can automatically select a B-mode slice of image data that includes the oscillating tip of the medical device. The selected B-mode slice is determined based on the Doppler data indicating movement of an object which is above a predefined threshold value, as is shown in FIG. 7B. The B-mode slice is selected by locating a maximum value within the Doppler data in the 3D echo data. The slice may also be selected based on other indicia associated with fast moving objects, such as the rate of change of the Doppler data within a particular region. For example, the B-mode slice may be selected based on a rate of change of 3D Doppler data such that, for example, a maximum slope indicates the fastest moving portion of the shaft (i.e. the tip 107). This is true regardless of whether the shaft and tip remain within the same B-mode slice.

As the shaft and tip move through the scan region, as defined by the scan head 703, the ultrasound scanner may be configured to identify and display the B-mode slice in which the maximum slope in the Doppler data occurs. Thus, the tip 107 of the medical device 103 may be tracked automatically as it is guided in vivo.

Figure 2:
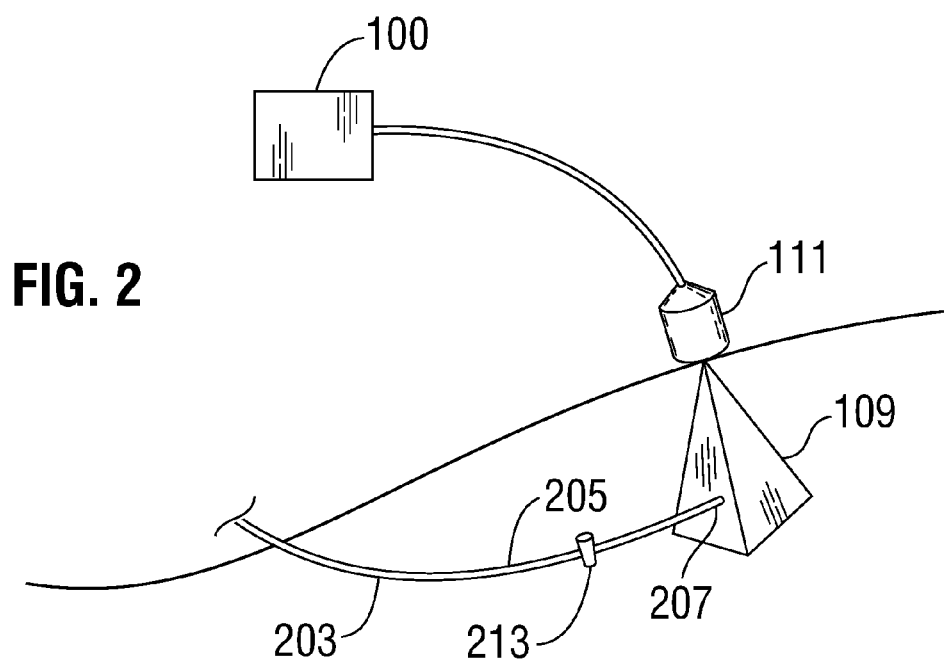
FIG. 2 schematically illustrates a system for locating the distal end of a medical device in vivo, with the device including a vibratory element that is inserted into the body.

FIG. 2 illustrates a medical device 213 having a modified configuration in which the vibration module 213 is affixed to the shaft 205 proximate to a distal end 207 thereof. One advantage provided by this configuration is that the vibration dampening effects of a cannula, if one is used, or surrounding tissues may be significantly reduced or eliminated. In this configuration, the vibration module 213 may be a small piezoelectric device that is configured to vibrate at a frequency chosen to suit the distal end 207 of the shaft 205. Specifically, the vibrational frequency of the piezoelectric device should be selected to correlate with a vibrational mode of the shaft to reduce the amount of vibrational dampening caused by the shaft itself. Thus when the shaft is in vivo, the distal end becomes more visible within the Doppler mode images displayed by the ultrasound scanner.

Figure 3:
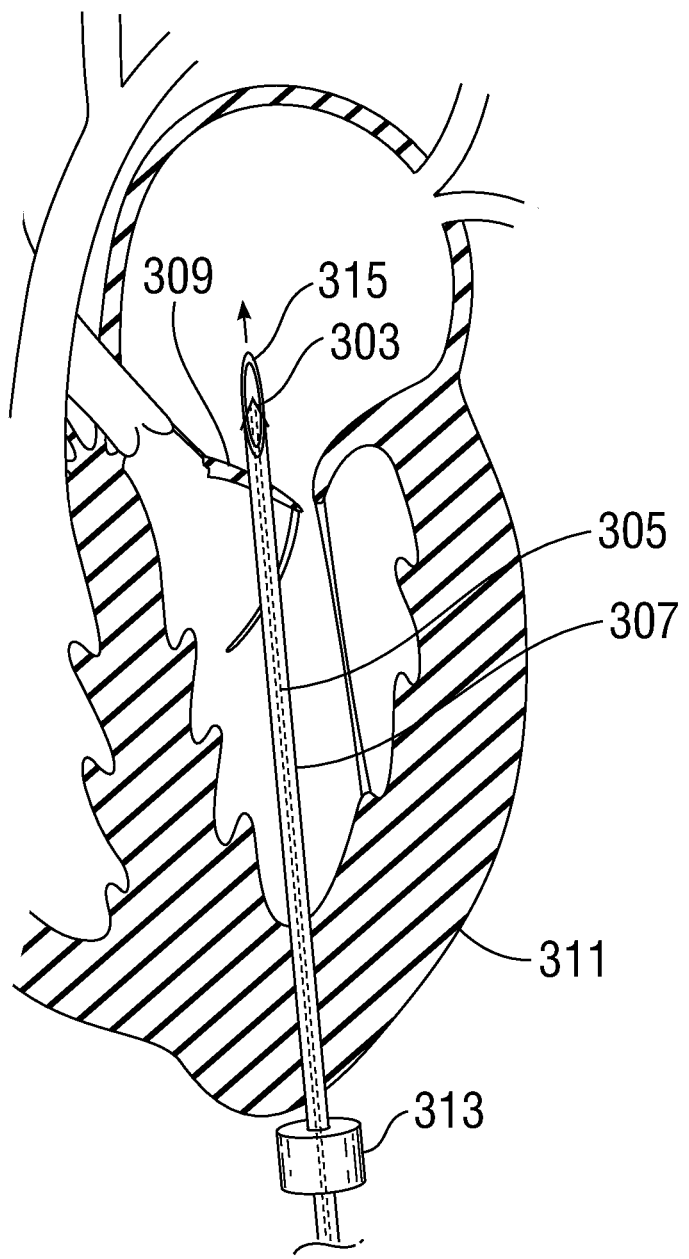
FIG. 3 illustrates the use of a needle applicator to place a neo-chord anchor for repair of a mitral valve.

An application for such a medical device is illustrated in FIG. 3. There, a neo-chord 303 and attached anchor 305 (shown in the closed position) are being inserted through a hollow needle 307 and placed to repair a damaged mitral valve leaflet 309 in a heart 311. This procedure may be performed by insertion of the needle through a small incision in the chest of a patient and up through the left ventricle into the heart, and it may be performed under beating heart conditions. A vibration module 313 is affixed near the distal end of the needle 307. Using an ultrasound scanner (either 2D or 3D) in Doppler mode, placement of the anchor 305 and neo-chord 303 are facilitated by providing visual guidance in the Doppler mode images. In particular, the Doppler mode of the ultrasound scanner may be color-adjusted so that the local maximum, i.e., that portion of the image representing the tip 315 of the needle 307, appears as a different color as compared to the shaft of the needle 307. Moreover, the coloration of the Doppler mode images may be further enhanced by adjusting the color so that the tip 315 also appears as a different color as compared to any hemodynamic flow, turbulence, or pressure, and to tissue movement in the localized vicinity, which in this example is the beating heart.

Figure 4:
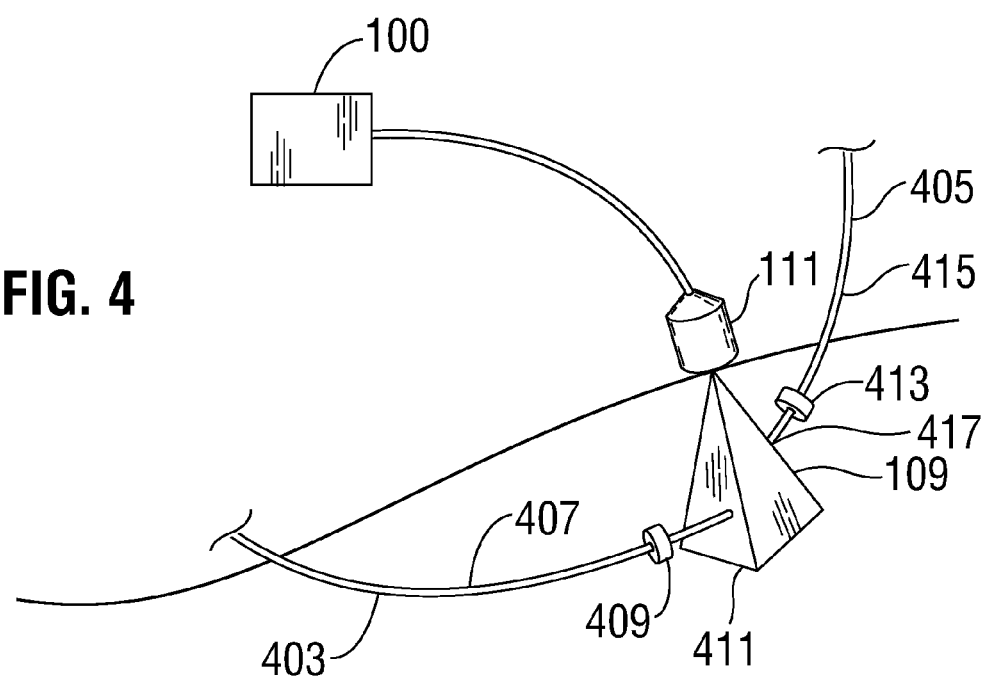
FIG. 4 schematically illustrates a system for locating the distal end of multiple medical devices in vivo.

FIG. 4 illustrates a system in which multiple medical devices 403, 405 are utilized and placed in vivo within the scan region 109 generated by the scan head 111 of the ultrasound scanner 100. As in FIG. 2, the first medical device 403 includes a shaft 407 and a vibration module 409 affixed proximate the distal end 411 thereof. Similarly, the second medical device 405 includes a vibration module 413 affixed to the shaft 415 at a distal end thereof 417. The positioning of the vibration modules 409, 413, whether proximate the distal ends of the respective shafts or at the proximal ends of the shafts, is a matter of design choice. It is expected that with some medical devices, it will be advantageous to use one configuration over the other based upon the design, materials, or usage of the medical device. In this system, the two medical devices 403, 405 may be vibrated using the same frequency, or they may be vibrated using different frequencies. The latter can provide an advantage in that Doppler mode images may be colorized to represent the two shafts 407, 415 using different colors, thereby allowing discrimination between the two shafts 407, 415 in Doppler mode images.

Figure 5:
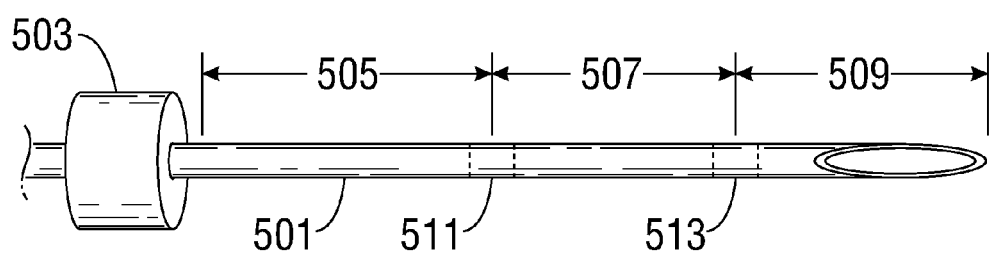
FIG. 5 illustrates the distal end of a medical device having varying densities.

FIG. 5 illustrates the distal end 501 of a medical device that is configured to vibrate at different rates. The vibration module 503 is affixed proximate the distal end 501, which is effectively divided up into three distinct different sections 505, 507, 509 by the inclusion of higher (or lower) density material to change the vibration frequency within each respective section. The first two sections 505, 507 are separated by the region 511, which is a region of composed of higher density material within the distal end 501. Alternatively, the entire section 507 could be formed from material of a different density to achieve similar functionality. The higher density material in this region serves to attenuate the vibrations generated by the vibration module 503, so that the two different sections 505, 509 can be displayed as different colors in Doppler mode images. Similarly, the last two sections 507, 509 are separated by the region 513, which is also a region of higher density material. Thus, these last two sections 507, 509 can also be displayed as different colors in Doppler mode images. The frequency of vibration generated by the vibration module 503, the materials with which the distal end are constructed, and the sensitivity of the Doppler mode for the ultrasound scanner should be matched in advance so that all three sections may be viewed as different colors in Doppler mode images.

This configuration shown in FIG. 5 can be useful when the medical device is a catheter and being used for positioning a balloon to open up a passageway. The balloon may be situated within the middle section 507, and the display of the different sections in different colors in Doppler mode images can be used to precisely position the balloon within the passageway.

Figure 6:
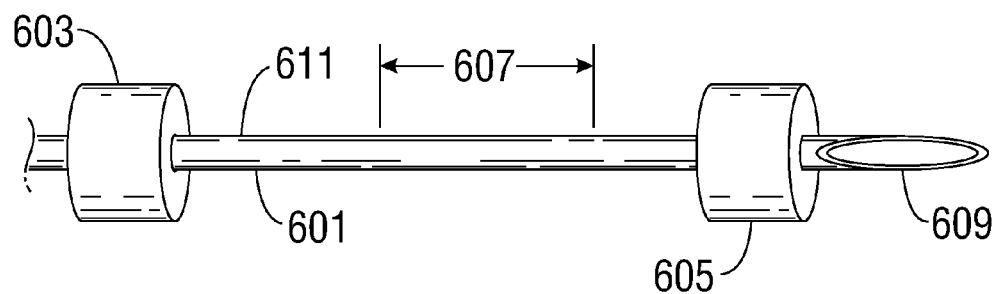
FIG. 6 illustrates the distal end of a medical device including multiple vibratory elements.

FIG. 6 illustrates the distal end 601 of a medical device that is configured with two vibration modules 603, 605. The two vibration modules 603, 605 are set to vibrate at different frequencies, so that the tip 609 can be made to vibrate at a different rate as compared to the proximal portion 611 of the distal end 601. To avoid vibrating the entire distal end 601 at a frequency resulting from constructive interference between the vibrations produced by the two vibration modules, 603, 605, a center portion 607 of the distal end 601 is constructed to dampen at least one of the two frequencies. With this configuration, the tip 609 and the proximal portion 611 of the distal end 601 can be displayed as different colors in Doppler mode images.

Figure 8:
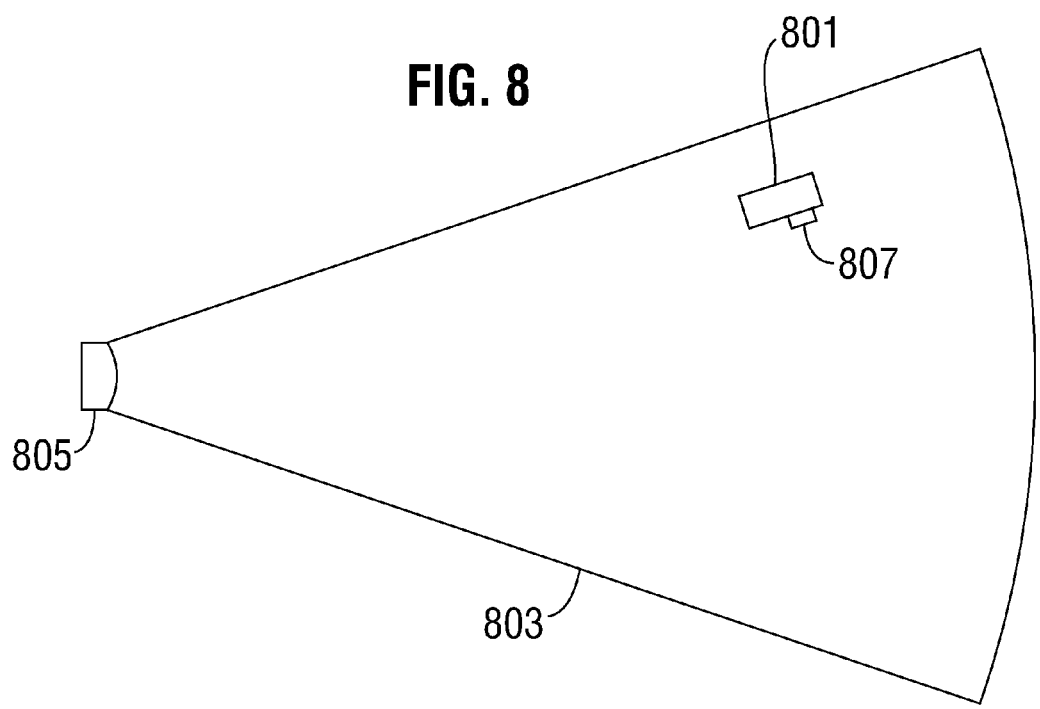
FIG. 8 schematically illustrates 2D ultrasound tracking, using Doppler mode, of an implanted medical device.

FIG. 8 illustrates a medical device 801 implanted into a patient and placed within the scan region 803 of a 2D ultrasound scan head 805. Optionally, a 3D ultrasound scan head, and corresponding ultrasound scanner, could be used. The medical device includes a vibration module 807 affixed thereto. Additional vibration modules may be attached as desired or necessary to account for device configuration, a need to identify different parts of the device in Doppler mode images with different colors, or for any other reason. The vibration module 807 includes its own power source and an RF receiver to enable activation and deactivation thereof. (Any of the vibration modules discussed above may include such features.) With the vibration module 807 affixed to the medical device 801, medical examinations and/or procedures may be performed as follow-ups to the implant procedure; such as identifying whether there are any potential problems with the implant, whether the implant remains properly positioned, whether the implant has retained its proper geometrical configuration, for removal of the implant, and the like.

Such independently powered and remotely activated medical devices can have many uses. One potential use is in the monitoring of certain disease conditions by the precise placement of vibrating medical devices to a particular anatomic region to detect a change in dimension over time. For example, placement of small, vibrating devices at the commissures of the mitral valve, as well as the anterior and posterior aspects, can permit monitoring of the mitral valve dimensions in the condition of functional mitral regurgitation.

As described herein, a vibrating medical device allows real time ultrasonographic visualization for the purposes of therapy, diagnosis, and monitoring of human illness. For example, the vibrating medical device can facilitate procedures on the open- or closed-heart to permit repair, replacement or implantation, of the aortic, mitral, pulmonic, or tricuspid valves. In particular, by applying the vibrating element to provide color contrast to that portion of a catheter bearing a balloon-expandable prosthetic aortic valve, precise positioning of the valve within the aortic annulus can be achieved under echo guidance. Further, to facilitate identification of wires or other forms of catheters—for example, a pig tail catheter—which may all be employed simultaneously, a vibrating element can be embedded within each respective device. Other procedures in which the vibrating medical device can be employed include all transcatheter approaches to mitral valve repair and replacement; valvular annuloplasty; insertion of new chordal apparatus, or Alfieri clip or suture devices; ventricular and atrial geometry modifying devices; repair of atrial septal defects and patent foramen ovale; occlusion or obliteration of the atrial appendage; insertion or removal of devices into the coronary sinus; the localization and creation of ablative lesions to the endocardium to treat atrial fibrillation or other electrical conduction abnormalities; positioning and deployment of intravascular stents (including, but not limited to, coronary, aortic, renal, carotid, subclavian, cerebral, and lower extremity arteries and veins) and angioplasty balloons, coronary rotoblators, atherectomy catheters, or perfusion devices; vascular filters (including venous thromboembolic filters and cerebral protection devices), where transvascular devices are utilized in the intact organ; and the like. Other specific devices include those described in U.S. Pat. Nos. 6,749,630; 6,726,717; 5,104,407; 6,182,664; 6,602,288; 5,879,366; 6,214,029; 5,108,420; 5,451,235; 6,723,038; 6,332,893; 6,402,680; 6,050,936; and 5,961,440; and in U.S. patent publication No. 2007/0112422.

Thus, a system and method for locating the distal end of a medical device in vivo are disclosed. While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A system for locating a medical device in vivo, the system comprising:
an ultrasound scanner having a scan head and being configured to operate in a 3D Doppler mode;

an elongated medical device having a distal end configured to be inserted in vivo, wherein the distal end comprises at least one cross-sectional segment having a different density as compared to adjacent cross-sectional segments; and a first piezoelectric vibratory element coupled to the medical device configured to induce vibrations in the distal end, wherein the distal end vibrates at a different frequency than the adjacent cross-sectional segments of different density, wherein when the scan head is positioned over the distal end inserted in vivo to obtain scan data of a tissue volume, the ultrasound scanner is configured to generate 3D Doppler data in the form of a plurality of slices from the scan data and to identify a location of the distal end within the slices based upon localized data within one of the slices meeting predetermined criteria.

2. The system of claim 1, wherein the first piezoelectric vibratory element is coupled to the elongated medical device near a proximal end that is not inserted in vivo.

3. The system of claim 1, wherein the first piezoelectric vibratory element is coupled to the medical device proximate the distal end.

4. The system of claim 3, further comprising a second piezoelectric vibratory element coupled to the medical device configured to induce vibrations in a medial section of the elongated medical device, wherein the medial section is configured to be inserted in vivo.

5. The system of claim 1, wherein the elongated medical device has three distinct sections, and each two adjacent sections are separated by a region composed of higher density material that attenuates the vibrations generated by the first piezoelectric vibratory element such that the distinct sections vibrate at different rates.

6. A method for locating a medical device in vivo, the method comprising:
 inserting a first distal end of a first elongated medical device in vivo, the first elongated medical device having a first piezoelectric vibratory element coupled proximate the first distal end to induce vibrations in the first distal end;
 inserting a medial section of the first elongated medical device in vivo, wherein a second piezoelectric vibratory element is coupled to the medial section to induce vibrations in the medial section;
 positioning a scan head of an ultrasound scanner over the first distal end and medial section placed in vivo to obtain scan data of a tissue volume;
 generating with the ultrasound scanner 3D Doppler data in the form of a plurality of slices from the scan data; and
 identifying locations of the first distal end and medial section within the slices based upon localized data within one of the slices meeting predetermined criteria.

7. The method of claim 6, wherein the first distal end comprises at least one cross-sectional segment having a different density as compared to adjacent cross-sectional segments.

8. The method of claim 6, wherein the predetermined criteria includes the localized data indicating movement of an object above a predefined threshold value within the slices.

9. The method of claim 6, wherein the predetermined criteria includes the localized data having a maximum rate of change within the slices.

10. The method of claim 6, further comprising
 inserting a second distal end of a second elongated medical device in vivo, the second elongated medical device having a second piezoelectric vibratory element coupled thereto to induce vibrations in the second distal end;
 positioning a scan head of an ultrasound scanner over the first and second distal ends placed in vivo to obtain scan data of a tissue volume; and
 identifying a location of the second distal end within the slices based upon localized data within one of the slices meeting predetermined criteria.

11. The method of claim 10, wherein the first and second piezoelectric vibratory elements are configured to operate at different rates of vibration.

12. The method of claim 6, wherein the piezoelectric vibratory element comprises a power source.

13. The method of claim 6, further comprising controlling the first piezoelectric vibratory element remotely through a radio frequency (RF) receiver included with the first piezoelectric vibratory element to enable activation and deactivation.

14. A system for locating a medical device in vivo, the system comprising:
 an ultrasound scanner having a scan head and being configured to operate in a 3D Doppler mode;
 a first elongated medical device having a distal end configured to be inserted in vivo; and
 a first piezoelectric vibratory element coupled to the first medical device proximate the distal end configured to induce vibrations in the distal end, wherein the first piezoelectric vibratory element comprises a power source and radio frequency (RF) receiver to enable activation and deactivation and is configured to be controlled remotely,
 wherein when the scan head is positioned over the distal end inserted in vivo to obtain scan data of a tissue volume, the ultrasound scanner is configured to generate 3D Doppler data in the form of a plurality of slices from the scan data and to identify a location of the distal end within the slices based upon localized data within one of the slices meeting predetermined criteria; and wherein the distal end of the first elongated medical device comprises at least one cross-sectional segment having a different density as compared to adjacent cross-sectional segments, such that the distal end vibrates at a different frequency than the adjacent cross-sectional segments of different density.

15. The system of claim 14, further comprising a second piezoelectric vibratory element coupled to the first elongated medical device configured to induce vibrations in a medial section of the first elongated medical device, wherein the medial section is configured to be inserted in vivo.

16. The system of claim 14, further comprising a second piezoelectric vibratory element coupled to a proximal end of the first elongated medical device that is not inserted in vivo and configured to induce vibrations in the first elongated medical device.

17. The system of claim 14, further comprising
 a second medical device having a second distal end configured to be inserted in vivo; and
 a second piezoelectric vibratory element coupled to the second medical device configured to induce vibrations in the second distal end, wherein the first and second piezoelectric vibratory elements are configured to operate at different rates of vibration.

18. The system of claim 14, wherein the first elongated medical device has three distinct sections, and each two adjacent sections are separated by a region composed of higher density material that attenuates the vibrations generated by the first vibratory element such that the distinct sections vibrate at different rates.

\* \* \* \* \*